United States Patent
Abbott et al.

(10) Patent No.: US 7,878,064 B2
(45) Date of Patent: Feb. 1, 2011

(54) ANALYTICAL APPARATUS WITH ARRAY OF SENSORS AND CALIBRATING ELEMENT

(75) Inventors: Julian Paul Abbott, Cambridge (GB); Klaus Wiehler, Hamburg (DE)

(73) Assignee: Akubio Limited (GB)

( * ) Notice: Subject to any disclaimer, the term of this patent is extended or adjusted under 35 U.S.C. 154(b) by 677 days.

(21) Appl. No.: 11/628,181

(22) PCT Filed: Jun. 9, 2005

(86) PCT No.: PCT/GB2005/002280
§ 371 (c)(1),
(2), (4) Date: Dec. 10, 2007

(87) PCT Pub. No.: WO2005/121769
PCT Pub. Date: Dec. 22, 2005

(65) Prior Publication Data
US 2008/0264170 A1    Oct. 30, 2008

(30) Foreign Application Priority Data
Jun. 12, 2004  (GB) ................................ 0413134.8
Oct. 2, 2004   (GB) ................................ 0421955.6

(51) Int. Cl.
*G01H 3/00* (2006.01)
(52) U.S. Cl. ...................................................... 73/590
(58) Field of Classification Search .................. 73/590; 422/68.1
See application file for complete search history.

(56) References Cited

U.S. PATENT DOCUMENTS

| | | | | |
|---|---|---|---|---|
| 4,817,066 A * | 3/1989 | Takasugi et al. | ............ | 367/137 |
| 5,144,262 A * | 9/1992 | Hunsinger | .............. | 331/107 A |
| 5,465,608 A | 11/1995 | Lokshin | | |
| 5,817,992 A | 10/1998 | D'Antonio | | |
| 6,149,190 A * | 11/2000 | Galvin et al. | ................ | 280/735 |
| 6,170,332 B1 * | 1/2001 | MacDonald et al. | ...... | 73/514.38 |
| 6,401,519 B1 | 6/2002 | McFarland | | |
| 6,990,852 B2 | 1/2006 | Berndt | | |
| 7,093,482 B2 | 8/2006 | Berndt | | |
| 7,621,028 B2 * | 11/2009 | Gelly et al. | ................. | 29/25.35 |
| 2001/0029774 A1 | 10/2001 | Grate | | |
| 2004/0038195 A1 | 2/2004 | Nerenberg | | |
| 2005/0037862 A1 * | 2/2005 | Hagood et al. | .............. | 473/345 |
| 2007/0046369 A1 * | 3/2007 | Schober et al. | ................ | 330/7 |
| 2007/0266799 A1 * | 11/2007 | Sugiura | ................. | 73/862.541 |
| 2008/0264170 A1 * | 10/2008 | Abbott | ........................ | 73/590 |

* cited by examiner

*Primary Examiner*—John Fitzgerald
(74) *Attorney, Agent, or Firm*—Barnts &Thornburg LLP

(57) ABSTRACT

Analytical apparatus for analysing at least one substance has an array of sensors (1) driven by an electronic driver (14) for operating each sensor. The signals produced by the sensors are received by a receiver (82), and the apparatus includes one or more calibration elements connected to the driver and the receiver for enabling changes in parasitic losses in the apparatus to be determined. The invention is particularly applicable to apparatus in which the sensors are electrical-mechanical transducers, individually connectable (in sequence) to the driver and receiver by a corresponding array of switches forming part of an interface (4).

35 Claims, 12 Drawing Sheets

ANALYTICAL APPARATUS WITH ARRAY OF SENSORS AND CALIBRATING ELEMENT

FIELD OF THE INVENTION

This invention relates to analytical apparatus for analysing a substance, which apparatus uses an array of sensors to that end. The invention also relates to a method of analysing a substance using such an array.

BACKGROUND TO THE INVENTION

The invention is particularly, but not exclusively, applicable to apparatus the sensors of which include piezo-electric and acoustic transducers, for example quartz crystal resonators.

Typically, each acoustic transducer has an active surface which is oscillated, and on which a receptor group is immobilised. The receptor group has chemical affinity or reactivity towards a substance to be detected or analysed. The substance to be analysed is normally suspended in a fluid which is brought into contact with the active surface. Physical, chemical and biochemical interactions between the receptor group on the surface and the substance cause a measurable change in mass attached to the surface and in other physical properties of the active surface, and these can be analysed to obtain qualitative and/or quantitative data on the substance.

Multiplexed assays using multiple sensing elements have found extremely broad utility in drug discovery, life sciences and diagnosis and academic research. The ability to carry out a number of measurements in parallel, or in rapid succession, enables a wide variety of ligand-target interactions to be screened. In addition multiple controls, or redundant positives can be included in an array, increasing the accuracy and reliability of the assay. Both high-density sensor arrays for high-throughput screening applications and lower-density arrays of sensors for various diagnostic applications have been employed to profile oligonucleotide expression levels and genetic mutation (i.e. DNA, cDNA, siRNA, miRNA and PNA chips) and to probe protein expression levels. This has allowed the diagnosis of genetic diseases, the genetic predisposition to various non-inherited diseases and both pre- and post-symptomatic diagnosis of diseases due to elevated or depressed levels of key protein biomarkers.

Due to the inherent complexity of biological systems, many diagnostic approaches now require a number of markers, or genetic sequences to be analysed. In drug discovery, many pharmaceutical companies have generated compound libraries with 100,000's to millions of compounds that need to be screened against a number of target receptors in an arrayed format. Arrayed sensor technologies are also being applied to new areas of proteomic and cellular analysis.

Such applications of sensor technology have generated the need to make measurements of different analytes on multiple identical receptors, where each sensor in the array may be brought into contact with a respective fluid sample. Alternatively, a single fluid sample may be conveyed to all of the sensors, each of which carries either a different respective receptor or group of receptors so that multiple tests are performed on the same sample. Applications of multiple analytes on multiple receptors are also known. An efficient means to achieve such types of measurements is to arrange the sensors in an array.

Each transducer may be connected, in turn, to a driver for oscillating the active surface. Signals from the sensor are received and processed at a receiver. The driver and receiver may, with the sensor, form part of an oscillator circuit with positive feedback so that the sensor is made to oscillate at the resonant frequency of that circuit, which frequency would be related to the mechanical resonant frequency of the sensor. Alternatively, the driver and receiver may form part of a network analyser which oscillates the active surface at a frequency which is swept through a range that includes the resonant frequency, and which analyses the frequency dependent admittance of the sensor over that range.

At least the latter type of apparatus, however, can suffer from a lack of high frequency stability and high system noise over practically useful timescales. One reason for the variability of the accuracy of the apparatus is the sensitivity to environmental and in particular thermal effects of the complete transducer-instrument system. Use of special cuts of transducer material such as AT-cut quartz and the use of reference transducers can minimise temperature dependence of the resonators, but this does not overcome the effect of the influence of temperature on the whole system and in particular on the interface between the instrument and the transducer. One particular effect that the applicants have found to limit the commercial development of robust systems using these technologies arises from the temperature dependence of parasitic losses. These arise from stray capacitance between active lines and ground, and distort the measurements made. As the operating frequency increases, the parasitic losses and their temperature dependence become more problematic, and cause drifts in the response of the system having characteristic timescales of 1-1000 seconds. As this is typically the timescale over which measurements are desired to be made, this has impeded development of this type of analytical apparatus.

Accuracy can be improved by monolithic integration of the sensor and interface electronics since this reduces the length of the various tracks, and hence parasitic loss effects. However, the production of such devices requires expensive capital equipment and may not always be practical, particularly as it is not straightforward to integrate discrete quartz/metal sensors into semiconductor device structures. This does not however solve the problem of changes in the variation of loss characteristics with temperature.

SUMMARY OF THE INVENTION

According to a first aspect of the invention, there is provided analytical apparatus for analysing at least one substance, the apparatus comprising an array of sensors, electronic drive means for operating each sensor, and a receiver for receiving and processing signals from the sensors, wherein the apparatus includes one or more calibration elements, also connected to the drive means and receiver, for enabling changes in parasitic losses in the apparatus to be determined.

Preferably, the calibration elements enable the parasitic losses, and hence any changes therein, to be determined.

Thus, the calibration elements provide data which can be used to compensate for the effects of parasitic losses, or of changes in such losses, on the sensor signals received by the receiver.

Each sensor may comprise any device which can be driven by a high frequency electrical signal and which has a resonant response dependent on contact with the substance or fluid.

Preferably, each sensor comprises a respective electrical-mechanical transducer having an active surface which is oscillated by the signal from the drive means, and which may to advantage carry an immobilised receptor group.

Preferably the transducer comprises a piezo-electric piezo-magnetic or acoustic transducer. Acoustic transducers include surface acoustic wave devices, bulk acoustic wave devices, surface transverse wave devices, acoustic plate mode devices, flexural plate mode devices, Love wave devices, surface transverse wave devices and Raleigh wave devices. The sensor element may be formed from any piezo-electric or piezo-magnetic material. Such materials are well known and include quartz, lithium tantalate, gallium arsenide, Zinc Oxide, polyvinylidene fluoride and the like.

Alternatively, the sensor may comprise a micro-electromechanical device, such as a membrane, a cantilever, a tuning fork, or other vibrating structure.

The sensor may be activated directly via the application of an oscillating voltage to the sensor (in the case of a Piezo-electric sensor) or by magnetically or electromagnetically activating the sensor.

The sensor may have two electrodes, one constituting the active surface, either of which may be earthed, or both of which may be at a floating potential.

Preferably, however, the active surface comprises an earthed electrode.

Such an arrangement avoids electrochemical effects between the active surface and the substance to be analysed (or any fluid which that substance is supplied to the sensors). However the invention can be used with either side earthed.

Preferably, each transducer comprises a quartz crystal resonator.

The drive means preferably comprises a common driver operable to provide power to the sensors and the calibration elements. This helps to ensure that the calibration elements and sensors are driven under substantially the same conditions.

Preferably, the driver and receiver are connected to the sensors and the calibration elements via a common interface.

Preferably, the common interface comprises a plurality of switches for enabling each sensor and each calibration element to be individually addressed by the driver and receiver. Preferably, each element and each sensor is connected to the driver by a respective switch.

Preferably, at least three calibration elements are provided, and all three are preferably passive circuit elements.

Preferably, to that end, a first of the calibration elements comprises a conductive path which provides a short circuit from the switch to earth, a second of the calibration elements comprises an open circuit, and the third of the calibration elements comprises a resistive load of a known finite resistance.

In order to provide the open circuit, the second calibration element may conveniently comprise a gap in a conductive track from the respective switch to earth. The track then corresponds to the conductive tracks connecting the sensors and the other calibration elements between the switches and earth, and therefore generates parasitic losses corresponding to those associated with the interface with the other calibration elements and the sensors.

Preferably, the calibration elements are situated at electrically analogous positions to the sensors.

This ensures that parasitic losses arising when the calibration elements are being driven, particularly losses from the interface, correspond to those arising when the sensors are driven. This feature thus facilitates the use of the signals from the calibration elements to correct for the contributions of parasitic losses to the signals received from the sensors.

To that end, the conductive paths from the driver to the calibration elements and the sensors are preferably of substantially the same length as each other. Furthermore, the length of the conductive paths from each calibration element and each sensor to earth (for example an earth bus) are also preferably the same length as each other.

The driver may to advantage be operable to drive each acoustic transducer at a frequency which is progressively varied over a range of possible frequencies, the receiver being operable to monitor a characteristic of the sensor impedance over said range.

This is potentially advantageous over an arrangement in which the driver, receiver and sensors form oscillator circuits since it is not necessary to wait for the system to "settle" at a resonant frequency. The sensors can therefore be addressed at a relatively rapid rate. The feature also enables inherent variation in the resonant frequency of each sensor to be accommodated.

The driver is conveniently operable to cause the oscillation frequency of each sensor to be swept through the resonant frequency of the sensor (when the latter is being addressed) the receiver being operable to monitor the admittance of the sensor over that range. The calibration element may be located on a printed circuit board which is separate from, but adjacent to, above or below the sensors. Such calibration elements may share the same ground plane and connector type as the switches. Alternatively, the calibration elements and sensors may be located on the same substrate. Such elements may be formed by thin or thick film deposition or integrated into a plane of the array.

Preferably, the switches are formed as a switching circuit in physical contact with or integrated into the array.

The array of sensors is preferably composed of a number of groups of sensors, each group being in a respective region of the array and having a respective one or more calibration elements, preferably in the same region, wherein the switches comprise one or more primary switches for selecting a group and a plurality of secondary switches for selecting a sensor or calibration element from the selected group.

This enables a large number of sensors to be operated by the same driver. Although the additional tier of switching increases parasitic losses, this is compensated for by the inclusion of the additional calibration elements.

The drive means and receiver may be constituted by a single unit, but are preferably separate components of the apparatus.

The invention also lies in a method of analysing one or more substances, the method comprising the steps of bringing the or each substance into contact with one or more sensors in an array of sensors, supplying electrical power to the sensors and receiving and analysing the signals received from the sensors, wherein the method further comprises the steps of periodically interrogating one or more calibration elements and analysing the signals received from said one or more calibration elements to provide data on at least the changes in parasitic losses in the circuitry connected to the sensors and using said data to compensate for the effects of said changes on the received output from the sensors.

Preferably, power is supplied to each sensor in turn in one cycle of operation and at least one calibration element is preferably interrogated once each cycle. Preferably, if the interrogation of said calibration element indicates a significant change in parasitic loss, one or more further different calibration elements are interrogated, preferably in the same cycle, to provide further data for that cycle.

BRIEF DESCRIPTION OF THE DRAWINGS

The invention will now be described, by way of example only, with reference to the accompanying drawings in which.

DETAILED DESCRIPTION

Figure 1:
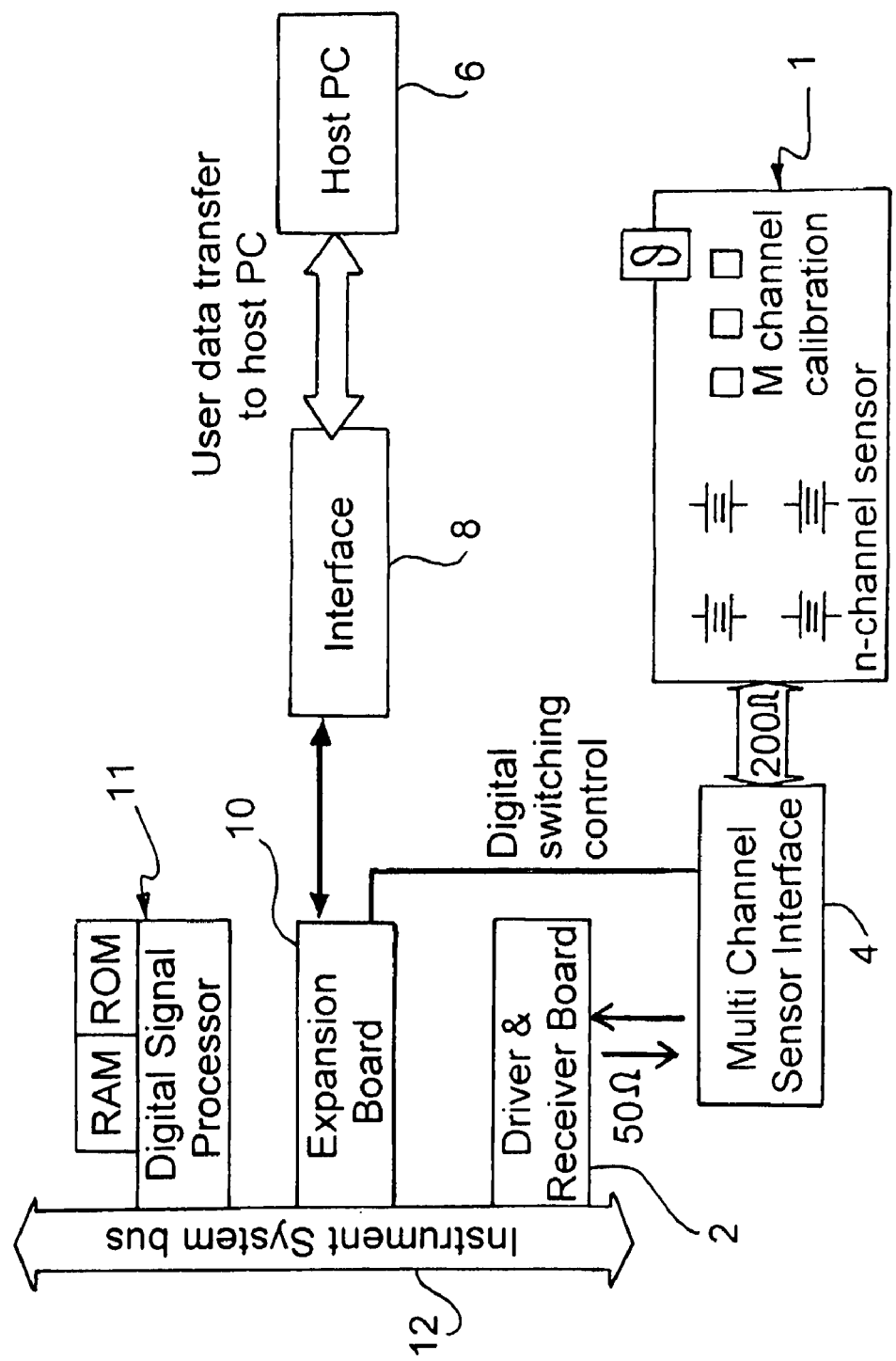
FIG. 1 is a schematic block diagram of an analytical system which includes apparatus in accordance with the invention.
Figure 2:
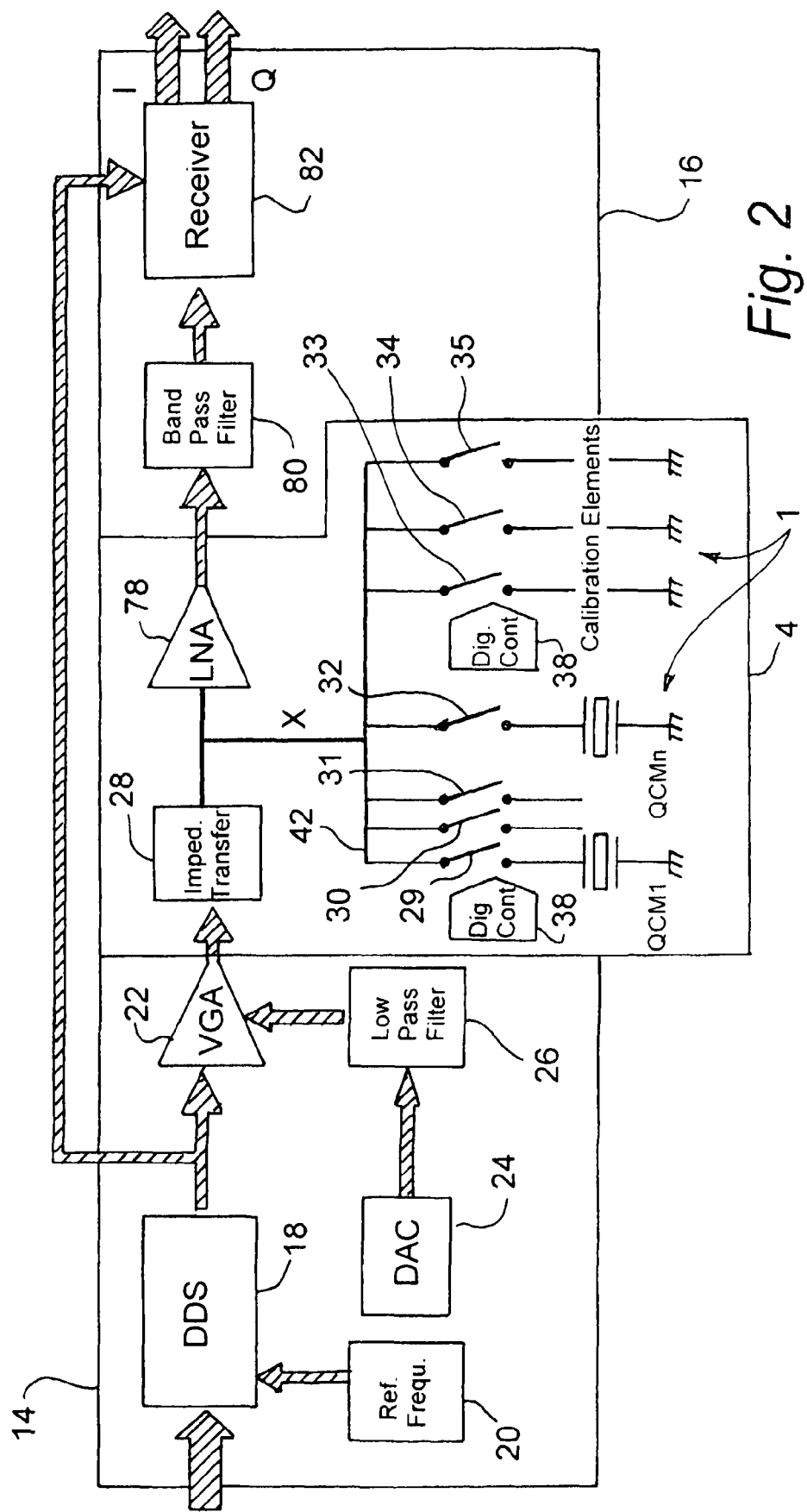
FIG. 2 is a block circuit diagram of said apparatus.

With reference to FIGS. 1 and 2, the apparatus according to the invention comprises an array of sensors and three calibration elements, all of which are denoted by general reference numeral 1. Each sensor can be individually connected to a driver and a receiver 2 via an interface 4, The operation of the instrument is controlled by means of a host PC 6 which sends instruction signals via interface 8 to expansion board 10. The expansion board 10 provides the digital control signals to a Digital signal processor (DSP) and controller board 11, which controls the operation of the instrument, such as timing, defining the settings, initiating the drive signals, receiving and processing the received digital signals from the sensors and calibration elements. The DSP is equipped with ROM in which is programmed in firmware the instruction sets for the instrument operation, and RAM sufficient for handling measurement data management and conversion in real time. Typically the DSP is a high speed CPU, many of which are well known in the art. The instrument digital system bus 12 carries all the data signals between the components of the system; the expansion board 10, the driver and receiver board 2, the digital signal processor 11 and the sensor interface 4. The driver and receiver board accepts digital control signals from the DSP, and generates analogue RF drive signals. These signals are applied via the interface 4 to the sensing and calibration elements. The interface 4 operates the switching of the driver and receiver to the sensor and calibration elements, under direct control of the PC 6. It also includes a circuit 28 (FIG. 2) which carries out the transfer of the impedance of the signals between standard 50 Ohm and the appropriate characteristic impedance of the sensor elements, in order to minimise power loss. The response signals are received by the receiver from the addressed sensor or calibration element and following impedance transfer back to 50 Ohms in the interface 4 are passed back to the driver and receiver board 2. This includes a fast ADC (not shown), which provides digital data for realtime analysis by the DSP 11.

Data generated is then passed back via the expansion board 10 and interface board 8 to the PC 6 for display, analysis and storage.

Figure 3:
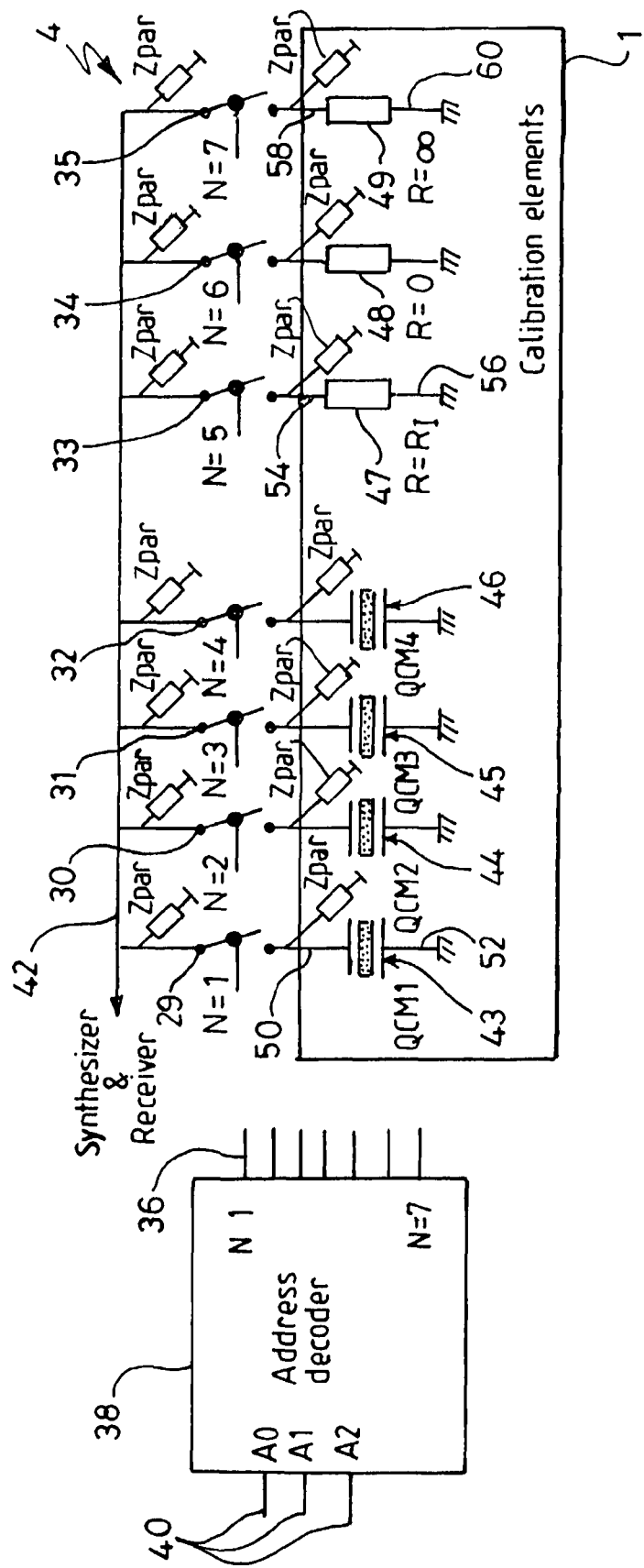
FIG. 3 is a more detailed diagrammatic view of the sensors, calibration elements and switches of the apparatus shown in FIG. 2.

The sensor array and calibration elements 1, driver and receiver board 2 and interface 4 are shown in more detail in FIG. 2 in which the driver and receiver are respectively denoted by reference numerals 14 and 16, and in FIG. 3

The driver 14 comprises a digital synthesizer 18 which receives a clock signal from an OCXO oven controlled crystal oscillator 20, and is operable, under the control of the PC 6, to generate a sinusoidal output signal of a continuously variable frequency. The range of frequencies over which the output signal is varied is controlled by means of the host PC 6, and the output from the synthesizer 18 is connected to a variable gain amplifier 22. The computer 6 sends a digital gain control signal to a digital to analogue converter 24, connected to the amplifier 22 via a low pass filter 26 so that the computer 6 also controls the level of the output signal from the amplifier 22. The output of the amplifier 22 is connected to the impedance matching circuitry 28 of the interface 4, which transfers the impedance of the signal path from the amplifier 22 to match the sensor interface impedance.

The interface 4 further comprises seven electronic switches 29 to 35, each of which is opened and closed by means of control signals received from a respective output line, for example line 36 of an address decoder 38. The decoder 38 has three input lines 40 through which the decoder receives from the computer 6 a multibit signal identifying the switch to be closed. The decoder 38 responds to such a signal by selecting the relevant output line along which to pass a signal for causing the selected switch to close, whilst ending any "close" signal that is being supplied through any of the other output lines. For the sake of clarity, the connection of the decoder 38 to the computer and each individual switch has not been shown in FIGS. 2 and 3.

When closed, each of the switches 29-32 connects an active rail 42 to a respective one of four sensors 43-46, and thus connects the selected sensor to the output of the driver 14 and to the input of the receiver 16. Each sensor comprises a quartz crystal resonator which is oscillated by the signal from the driver 14 (at the frequency of the driver signal) Each resonator has an active surface, which is part of the earthed electrode of the resonator. The other electrode, the driven electrode, is in use connected to the output of the driver 14. The active surface carries an immobilised receptor group relevant to the analysis to be performed by the resonator. Each of the resonators carries a respective receptor group to enable four different tests to be conducted on a single sample.

Each of the switches 33, 34 and 35 is operable to connect the driver 14 and receiver 16 to a respective one of three calibration elements 47-49 via the rail 42. Each calibration element is also connected to earth.

The calibration element 47 is a resistor of a known resistance, for example in the case of a quartz crystal transducer this would be 200 Ohms, which is the motional impedance of the sensor under a liquid load, but could be different depending on the characteristic impedance of the sensor used and its load. The element 48 consists of a low resistance conductive track providing a short circuit to earth, whilst the element 49 takes the form of a break in the conductive track from the switch 35 to earth, and is therefore, in effect, a resistor of infinite resistance.

The driven electrode of the resonator 43 is connected to the output of the switch 29 by means of an input track 50, and the active surface of that sensor is connected to earth via a track 52. An identical arrangement of tracks connects each of the active terminals of the sensors 44, 45 and 46 to the switches 30, 31 and 32 respectively and the active surfaces to earth.

One side of the calibration element 47 is connected to the output of the switch 33 by a track 54 of the same length as the track 50 and hence the corresponding tracks for the other sensors, the other side of the element 47 being connected to ground through a track 56 of the same length as the track 52 (and the corresponding tracks for the other sensors). As far as the circuit break 49 is concerned, the length of track from the output of the switch 35 to that break is the same as that of the track 54, whilst a track 60 runs from the other side of the break to ground and is also the same length as track 56.

The calibration element 48 is indistinguishable from its connecting track, but the overall length of the element 48 and the tracks (i.e. the distance between the output of the switch 34 and the ground plane) is the same as the distance from the output of any of the other switches to the ground plane.

In addition, the conductive tracks connecting the rail 42 to the input of each of the switches 29-35 are of substantially the same length as each other. Thus, the calibration elements 47-49 are in positions which are analogous to those of the sensors 43-46 so that the parasitic impedance of the interface 4 (indicated by the impedances $Z_{par}$) is the same for the calibration element as for the sensors.

Figure 4:
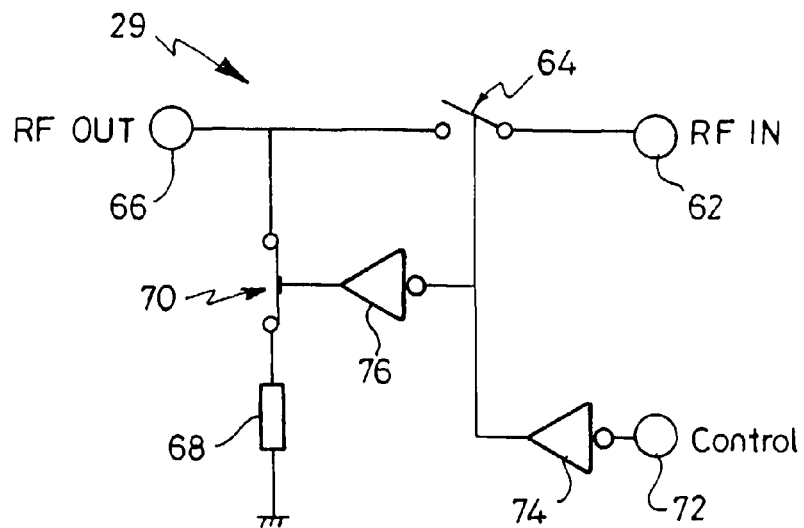
FIG. 4 is a more detailed schematic view of one of said switches.

The switch 29 is shown in more detail in FIG. 4. Since the switches 29-35 are identical, only the switch 29 will be described in more detail.

With reference to FIG. 4 switch 29 has an input 62 which connects one side of a transistor switch 64 to the rail 42. The other side of the switch 64 is connected to an output 66 which is in turn connected to the line 50. The same side of the switch 64 is also connected to earth via a resistor 68 and a second transistor switch 70. The value of resistor 68 is defined by the requirement to match the load impedance on the sensor, as this provides maximum power dissipation to the sensor when switched to the inactive state. Thus for a liquid load a 200 Ohm resistor is preferable, but in practice a standard value such as 50 or 75 Ohms is effective. Different resistances may be used for other types of sensor. A control signal input 72 provides a connection from the line 36 of the address decoder 38 to a first NOT gate 74. The output of the NOT gate 74 supplies a control signal to the switch 64 and an input to a second NOT gate 76, the output of which provides a control for the switch 70. Thus, when there is a voltage on the line 36, the switch 64 is held open by a signal from the gate 74, whilst the gate 76 holds the switch 70 closed. In this condition, the switch 29 is open so that the sensor 43 is isolated from the driver 14 and the receiver 16. At the same time, the driven electrode of the sensor 43 is actively terminated by the connection to earth through the resistor 68. When an inactive sensor is adjacent to an active one it will tend to oscillate due to coupling. This can cause interference and spurious signals on the outputs, and to reduce this the active electrodes of the sensors are therefore terminated when those sensors are not being operated. As a result, those sympathetic oscillations are prevented from interfering with the analysis circuit while the response of the selected active resonator is being measured.

Alternatively, the switches 64 and/or 70 may be physical switches which make and break the connections, such as relays or micro-electromechanical devices. They may be solid state devices capable of operating in this way such as CMOS, GaAs, or Silicon on insulator structure. CMOS structures have the advantage of low cost, while GaAs may be used in higher frequency applications. Solid state based devices may be comprised of a diode for example. Other switches are known in the art.

The receiver 16 has a low noise amplifier 78 which amplifies the signal received from the active sensors/calibration element via the rail 42. The output of the amplifier 78 is fed via a band pass filter 80. This has a bandwidth of typically 500 kHz centred around the nominal resonant frequency of the sensor elements, and has the function of eliminating 1/f noise at low frequencies and also spurious resonant mode signals arising from the transducer at frequencies above the measured resonance. Depending on the characteristics of the receiver this may be replaced by a low pass filter only, or may not be needed. The receiver element 82 is a mixer, which receives the drive signal directly from the DDS 18, and mixes this with the received signal from the sensor element. This may be done in a variety of ways, either digitally or analogue. In the analogue domain shown here the receiver produces a 90 degree phase shifted signal from the drive signal, and carries out two mixing operations one with the in phase drive and one with the in quadrature drive signal to produce an in-phase and in quadrature DC signal. This fully characterises the complex voltage ($V_x$) response of the sensor during the frequency scan., as discussed below.

Figure 5:
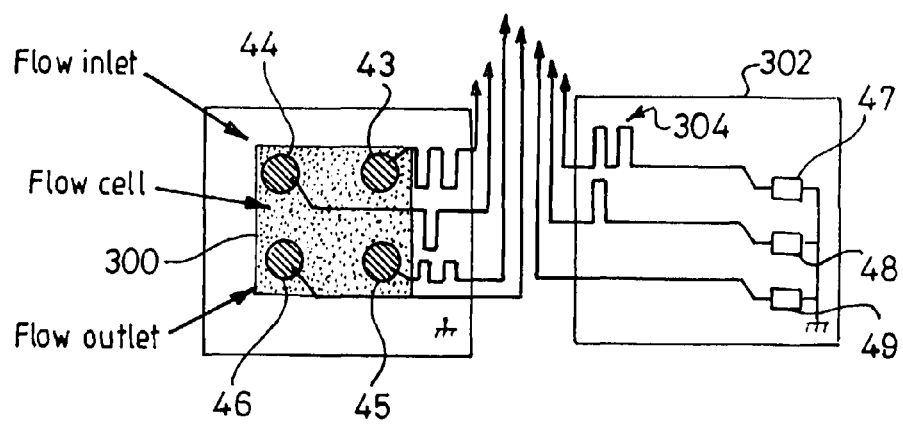
FIG. 5 is a plan view of the physical layout of the sensors and calibration elements of the apparatus, the sensors being included in a flow cell.
Figure 9:
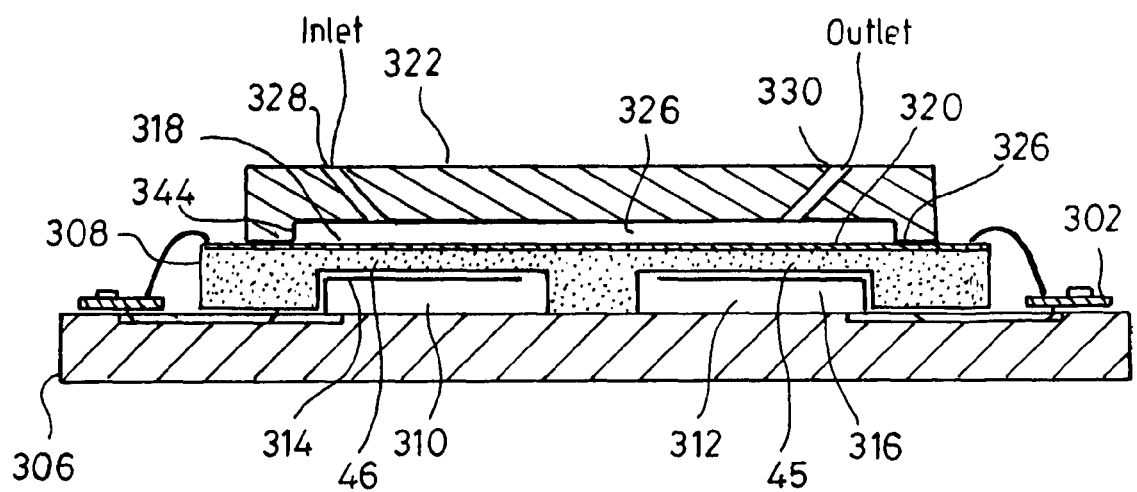
FIG. 9 is a cut away side view of the flow cell shown in FIG. 5.

With reference to FIGS. 5 and 9, the four sensors 43-46 are provided in a flow cell 300, whilst the calibration elements 47-49 are provided on a separate PCB 302. A respective one of four receptors (not shown) is immobilised on each sensor, so that the sensors perform four different types of analysis on a sample passing through the flow cell. Each of the sensors 43-46 and elements 47-49 is connected to its respective switch (29-35) via a respective track. All of these tracks are of the same length, which is why some of the tracks (eg for the elements 47, 48 and sensors 43-45) have serpentine portions (eg. 304). The flow cell 300 comprises aluminium base block 306 which is thermally coupled to a Peltier cooling system (not shown), and which supports a quartz plate 308, the underside of which has four circular recesses for example 310 and 312, each corresponding to a respective sensor. The driven electrode, for example either of the electrodes referenced 314 and 316, for each sensor is coated onto the underside of the plate 308 in the respective recess. The earthed electrodes, for example electrodes 318 and 320, are coated onto the upper surface of the plate 308 in a position in which each opposes the underlying driven electrode on the underside of the plate. In use, the relatively thin regions of quartz between the two electrodes of each sensor acts as the resonating part of the sensor whilst thicker layer of quartz (i.e. the portions the plate surrounding the recesses) acts as a support which also helps mechanically to isolate the sensors from each other. The upper electrodes of the sensor are overlaid by a top plate 322 which is rectangular, when viewed in plan, and includes a rectangular peripheral wall 344 which defines a flow cavity 326 between the plate 322 and the upper surface of the quartz plate 308. The upper plate may be machined or moulded from any suitable plastics material, preferably a bio-compatible polymer such as polyethylethylketone (PEEK) attached to the quartz plate by a compliant adhesive 326 under which the conductive tracks for the electrodes on the upper surface of the plate 308 extend to enable those electrodes to be connected to earth via wires connecting the tracks to the earth strip of the PCB 302.

The circuit board 302 is mounted adjacent to the housing, and may be conventional or ceramic or integrated into the lower housing block.

The upper plate 322 has an inlet 328 and an outlet 330 for the sample of liquid to be passed through the flow cavity 326 to be analysed by the sensors.

In another embodiment of apparatus in accordance with the invention the single flow cell arrangement shown in FIGS. 5 and 9 is replaced by two adjacent flow cells separated by a barrier depending from the centre of the plate 322. The plate 322 is also provided with an additional inlet and outlet so that each flow cell has a respective inlet and outlet.

In this case each flow cell contains a reference sensor (as described below) and a sensor on which a respective receptor has been immobilised.

The aluminium block is thermally controlled by means of the peltier cooling system. The temperature of operation may be chosen depending on the application. One or more thermocouples may be placed conveniently close to the flow cell to enable the temperature stability of and variation within the flow cell to be monitoried and the peltier system to be controlled accordingly. Thermal fluctuations of the cell are another source of noise and drift in the measurement which must be minimised using the peltier system. Residual temperature dependent drift of the system has been observed to be ~20 Hz/deg C. After elimination of the temperature dependent response of the quartz crystal sensor, the remaining frequency variations are believed to arise from the temperature dependence of physical properties of the materials in the fluids (and of the fluids themselves) and the cell which influence the resonant properties of the sensor. Peltier cooling can achieve a temperature stability of 0.01° C. and this is believed to limit these variations to ~0.3 Hz. Variations on this arrangement could include more than one peltier element to stabilise larger arrays when enclosed in an instrument casing. Monitoring of the temperature is carried out by the PC, and can include warnings in the case of excursions over a defined threshold. In order to achieve this level of control it is advantageous to ensure that other components of the system are thermally stabilised also, for example the fluid and the circuitry, to minimise the effect of the immediate environment on the sensor.

It will be appreciated that this level of temperature control may not be necessary for other embodiments of the invention.

The flow cell may be of any design used in the art depending on the application. For example FIG. 1 in WO0212873 shows a common design where the sensor element is disposed between two O-rings, and FIG. 2 an improved design where the element is immobilised by a compliant adhesive on the periphery of its inactive surface. Array structures may be fabricated using discreet sensor elements as disclosed in this application, and optionally constructed to mate with standard ISO well plates, for example 96, 384 and so on. Smaller scale arrays can be fabricated from single quartz substrates, where individual sensor elements are fabricated by etching a thin resonator into a thicker plate of quartz, the latter areas acting as a mechanical support. Structures of this type and methods of fabrication are disclosed for example in J Rabe et al; IEEE Sensors J. 3, 361 (2003). FIG. 9 shows a cross section of a 2×2 array using the etched structures of this publication. The chemically active earthed electrode of each sensor support 301 is earthed to the housing by the use of a compliant adhesive, and connection with the driven electrode is made via insulated channels in the base of the plate 306. These are then taken to the circuit board 302 plate which may be conventional or ceramic or integrated onto the lower housing block and which comprises the track layout shown in FIG. 5, the calibration elements, and connectors to the drive and measurement units. Such an arrangement is scaleable to smaller sensors in larger arrays, where several sets of calibration elements may be disposed around the perimeter of the sensor array, and the sensors switched using the hierarchical arrangement of FIG. 7, described below.

In use, an analyte fluid is passed into the flow cell, and each of the sensors 29-32 is operated in the way described below.

The computer 6 selects the relevant sensor and sends a suitable signal to the decoder 38 to cause the switch for that sensor to close. The computer also causes the synthesizer 18 to generate a sinusoidal signal at a starting frequency and then progressively to increase the frequency to a given maximum. The range of frequencies spanned is intended to include the resonance frequency of the sensor (and any substance bound onto the receptors immobilised thereon). As the variable frequency signal is fed to the sensor, its admittance is measured by the receiver 82, and this is stored in the computer 6 as a function of frequency. The admittance can be used to provide a measurement of the resonance frequency of the sensor, and/or the Q factor of the sensor (with the bound substance) in the fluid medium. For example, the frequency at which the admittance is at a maximum will correspond to the resonance frequency of the sensor since it is at this frequency that the sensor will accept the maximum amount of driving energy from driver 14. The process is repeated for each of the sensors 44, 45 and 46 and then each of the calibration elements 47-49 is interrogated in turn. The interrogation of the final calibration element marks the end of one cycle of the operation of the apparatus, and the process can then be repeated.

In a preferred embodiment at least one of the sensors may be a reference sensor. By this is meant that receptor immobilised on the surface of the sensor element has no affinity for an analyte species and thus will not bind any analyte and generate added mass, but in all other respects the sensor element, cell and fluid is the same as other sensors and flow cells. Because the resonance frequency and Q of a quartz crystal sensor element depends on fluid properties as well as attached mass, this enables the influence of the fluid properties to be removed from the response of sensing elements which carry receptors and are exposed to the same fluid, and a measurement of the amount of attached mass isolated. In practice, before measuring the admittance characteristics of the sensor array under the analyte containing fluid, the correct frequency scan range for each resonator is determined. This can be done using an iterative approach: starting with a broad frequency scan of say 500 kHz centred around the normal resonance frequency of the given sensor (i.e. when no substance is bound onto the receptor, and the sensor is in a buffer fluid) data is collected at a number of frequencies. This is fitted against well-known equations to determine rough estimates of the actual resonance frequency and quality factor or resistance and inductance associated with the sensor. The scan range is then narrowed, using this data, and the process is repeated to get improved estimates of resonance frequency, Q (equivalent to Resistive and Inductive load) By repeating with narrower frequency ranges the estimates approach constant values and this can be used to calculate the optimum sweep range for each resonator. The resonant frequency can then be determined by fitting the data in this narrow range to a physical model of the resonance. In general resonators will have slightly different resonances and Q factors, and thus different sweep ranges. The range for each resonator is stored in the control software for use in the measurement phase. During this base line measurement, calibration measurements may also be made. The calibration data is collected over the range of frequencies which encompasses all the different frequency ranges of the resonators in the array. Because of the variation in the resonator sweep ranges the calibration sweep range is typically wider than any of the resonator ranges. With a fixed number of data points generated by the network analyser in all sweeps, the frequencies of the datapoints in the wider calibration sweep will not align precisely with that of the resonators. In order to calibrate accurately at each point in an individual resonator sweep it is then necessary to interpolate the calibration data. Because of the closeness of the frequency points a linear interpolation is usually satisfactory, but other algorithms may be used. The interpolated calibration data is then used to calibrate the resonator at each frequency datapoint as described below.

During the fitting step, in theory, a minimum of two frequency datapoints per channel (i.e. calibration element or sensor) can be used to obtain the necessary fit, but in practice a larger number can improve accuracy.

The sensors are then addressed sequentially to make appropriate measurements.

Although, in the example described above, each calibration element is addressed/interrogated once per operating cycle, other sequences of operation may be applied, for example, the sensor 43 can be addressed initially, and then each calibration element 47-49 can be addressed in turn. While the true admittance characteristics of the sensor 43 (i.e. correcting for variations in parasitic impedance) are made, the sensor 44 can be addressed and then each of the three calibration elements can be addressed/interrogated a second time. The process is repeated so that calibration data is obtained four times in every cycle of operation of the apparatus. By this means, the parasitic losses and impedance drift noise can be compensated for in real time.

Alternatively, certain calibration elements may be identified as indicators of drift or noise and these could be measured after each resonator measurement, and only if any significant change is detected would this trigger a measurement of all of the calibration elements.

In general, calibration readings should ideally be made on a timescale that is much less than the characteristic scale of the noise attributable to variations in the parasitic impedances. The applicants have found that the characteristic timescales of such noise (or impedance drift) to be typically around ten seconds. A dedicated network analyser such as the driver 14 and receiver 16 is capable of typically 12000 measurement points per second. With a scan of typically 100 points per channel (i.e. per sensor/calibration element) it is possible to achieve a reading rate of 120 channels per second. Depending on the number of channels in the array, it is therefore possible to make calibration measurements in less than approximately one second, which is a rate suitable to compensate for the temperature induced drift of the parasitic effects. Consideration of the analyser rate and number of points per channel is likely to enable the appropriate calibration rate for the number of transducers and environmental conditions to be determined. Alternatively, the duty cycle between resonators and calibration elements may be varied, for example by making calibration measurements after every second or every fourth resonator reading (or any other suitable interval).

The equivalent circuits shown in FIGS. 6 A-D are equivalent circuit diagrams modelling the parasitic losses and (with the following description) illustrating how the measurements of the voltage signals when the calibration elements are addressed can be used to correct for those losses. The meanings of the symbols used in those calculations are as follows:

$V_G$: is equivalent generator voltage, i.e. the voltage applied by the driver 14 to the interface 4

Figure 6A:
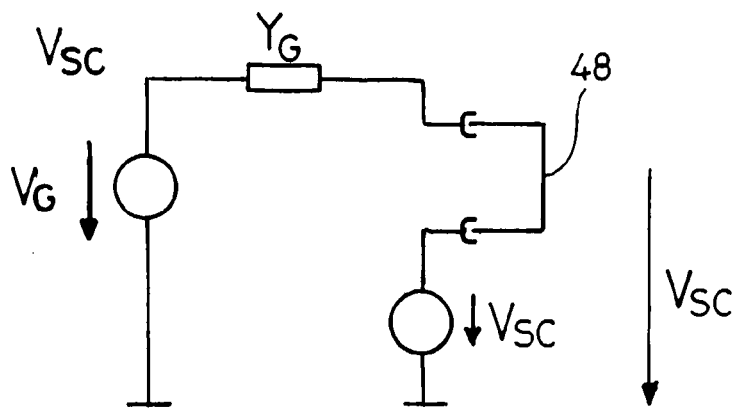
FIGS. 6A-6D are equivalent circuit diagrams which illustrate the calibration process.

$V_{SC}$: is the measured voltage for short circuit (FIG. 6A)

Figure 6B:
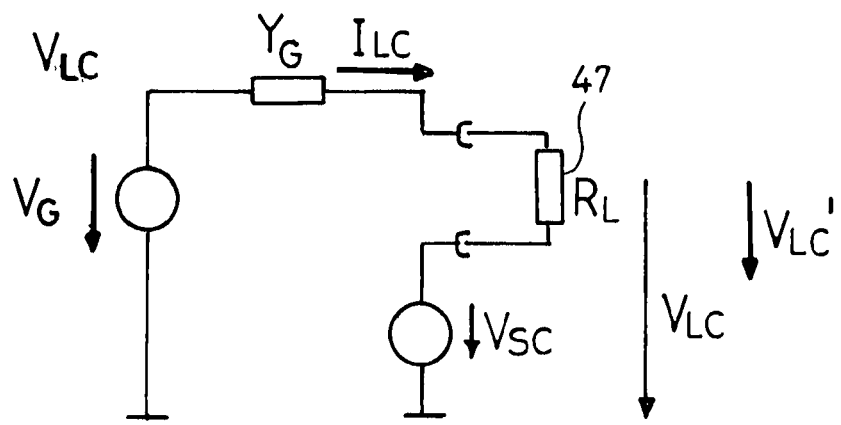

$V_{LC}$: is the measured voltage for loaded circuit (FIG. 6B)

Figure 6C:
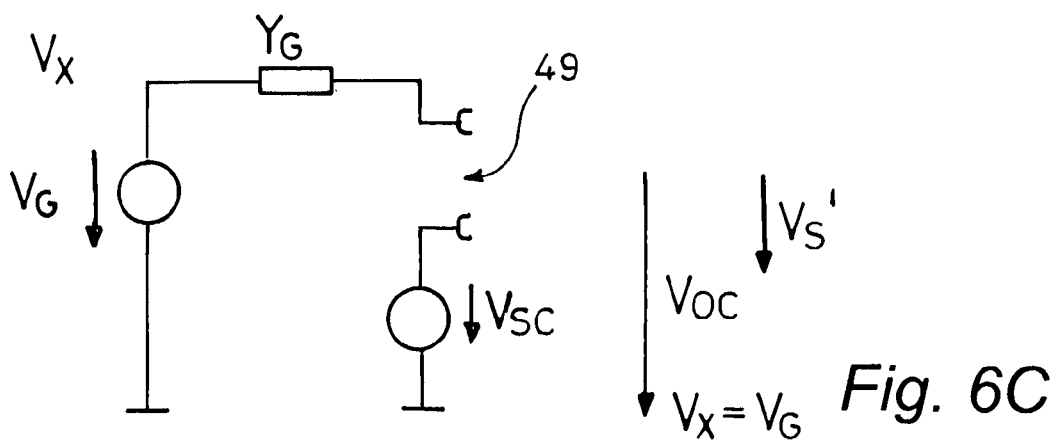

$V_{OC}$: is the measured voltage for open circuit (FIG. 6C)

$V_G^1$: is the voltage 'seen' at the sensor/calibration element ($=V_G-V_{SC}$)

$V_G^1 = V_{OC} - V_{SC}$ since $V_G = V_{OC}$ $Y_G$=equivalent generator admittance $Z_G$=equivalent generator impedance $R_L$ is the calibrated load resistor (e.g $R_L$=200 ohms)

$R_x/Z_x$ is the unknown resistor/impedance $V_{LC}^1$ is $V_{LC}$ corrected by the constant offset $V_{SC}$ $V_{LC}^1 = V_{LC} - V_{SC}$ $V_G^1$ is $V_G$ corrected by the constant offset $V_{SC}$ $V_G^1 = V_{OC} - V_{SC}$; $V_G = V_{OC}$ $V_X$ is the measured voltage for an unknown resistor $R_X$ $V_X^1$: $V_X^1 = V_X - V_{SC}$ (ie the voltage seen at the sensor)

Figure 6D:
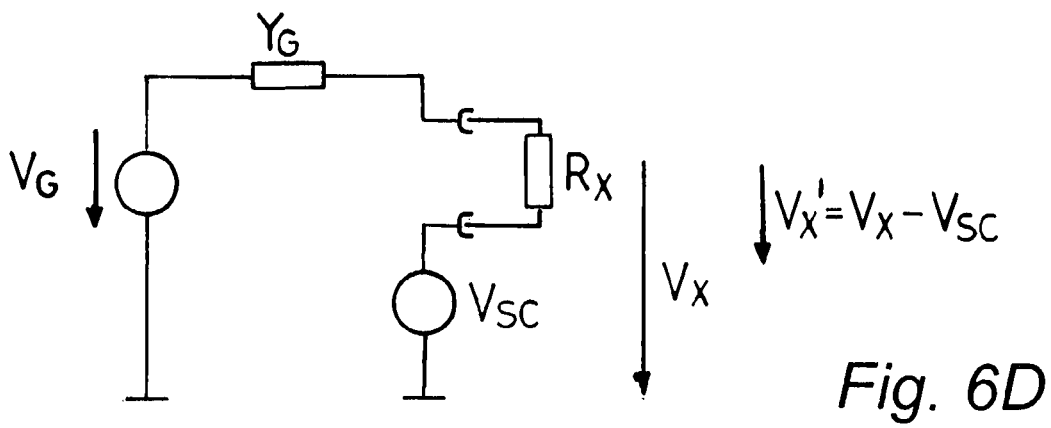

Calculation of $$Y_G = \frac{1}{Z_G}$$

when the load 47 is addressed, the current $I_{LC}$ in the circuit (FIG. 6B) is given by:

$$I_{LC} = \frac{V_G^1}{Z_G + R_L} = \frac{V_{LC}^1}{R_L}$$

therefore $$Z_G = R_L\left(\frac{V_G^1 - V_{LC}^1}{V_{LC}^1}\right)$$
$$= R_L\left(\frac{V_G - V_{LC}}{V_{LC} - V_{SC}}\right)$$
$$= R_L\left(\frac{V_{OC} - V_{LC}}{V_{LC} - V_{SC}}\right),$$

since $V_G^1 = V_{OC} - V_{SC}$ and $V_G = V_{OC}$ $$Y_G = \frac{1}{R_L}\left(\frac{V_{LC} - V_{SC}}{V_{OC} - V_{LC}}\right)$$

with reference to FIG. 6D $$\frac{V_X^1}{R_X} = \frac{V_{GS}^1}{Z_G + R_X}$$

therefore $$Z_X = Z_G \frac{V_X^1}{V_G^1 - V_X^1}$$

therefore $$Y_X = Y_G \frac{V_G^1 - V_X^1}{V_X^1} = Y_G \frac{V_G - V_X}{V_X - V_{SC}}$$

and $$Y_X = Y_G \frac{V_{OC} - V_X}{V_X - V_{SC}}$$

It will be appreciated that all calculations are done, in the complex domain, in view of the reactive components of some of the impedances.

Accordingly $$Y_G = \frac{1}{R_L}\left(\frac{V_{LC} - V_{SC}}{V_{OC} - V_{LC}}\right),$$

and the true value of the unknown sensor admittance is then given by $$Y_X = Y_G\left(\frac{V_O - V_X}{V_X - V_{SC}}\right),$$

where $V_X$ is the measured voltage across the sensor.

Figure 7:
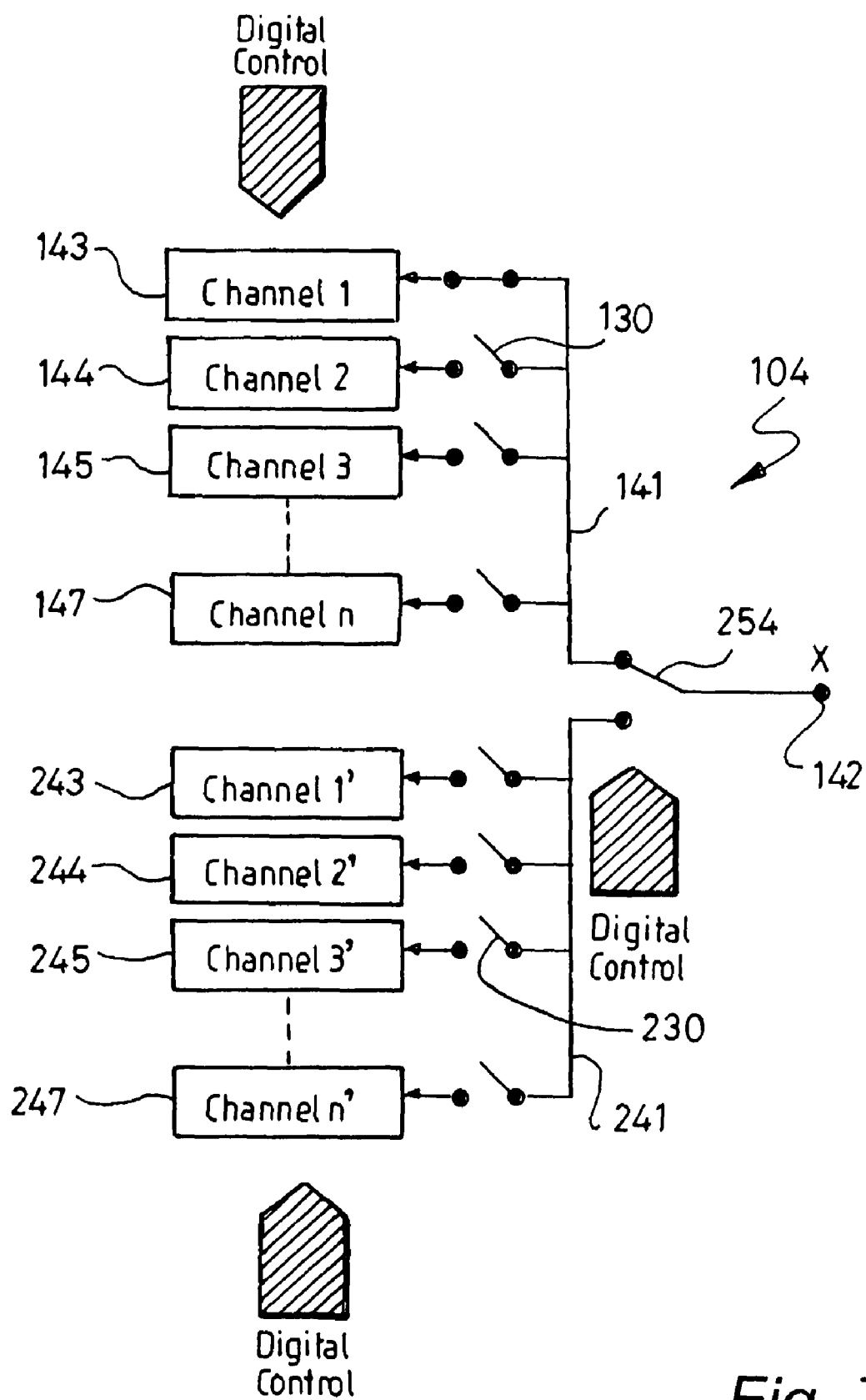
FIG. 7 is a block diagram of a modified version of the apparatus, in which there is provided two arrays of sensors, each array having its own set of calibration elements.
Figure 8:
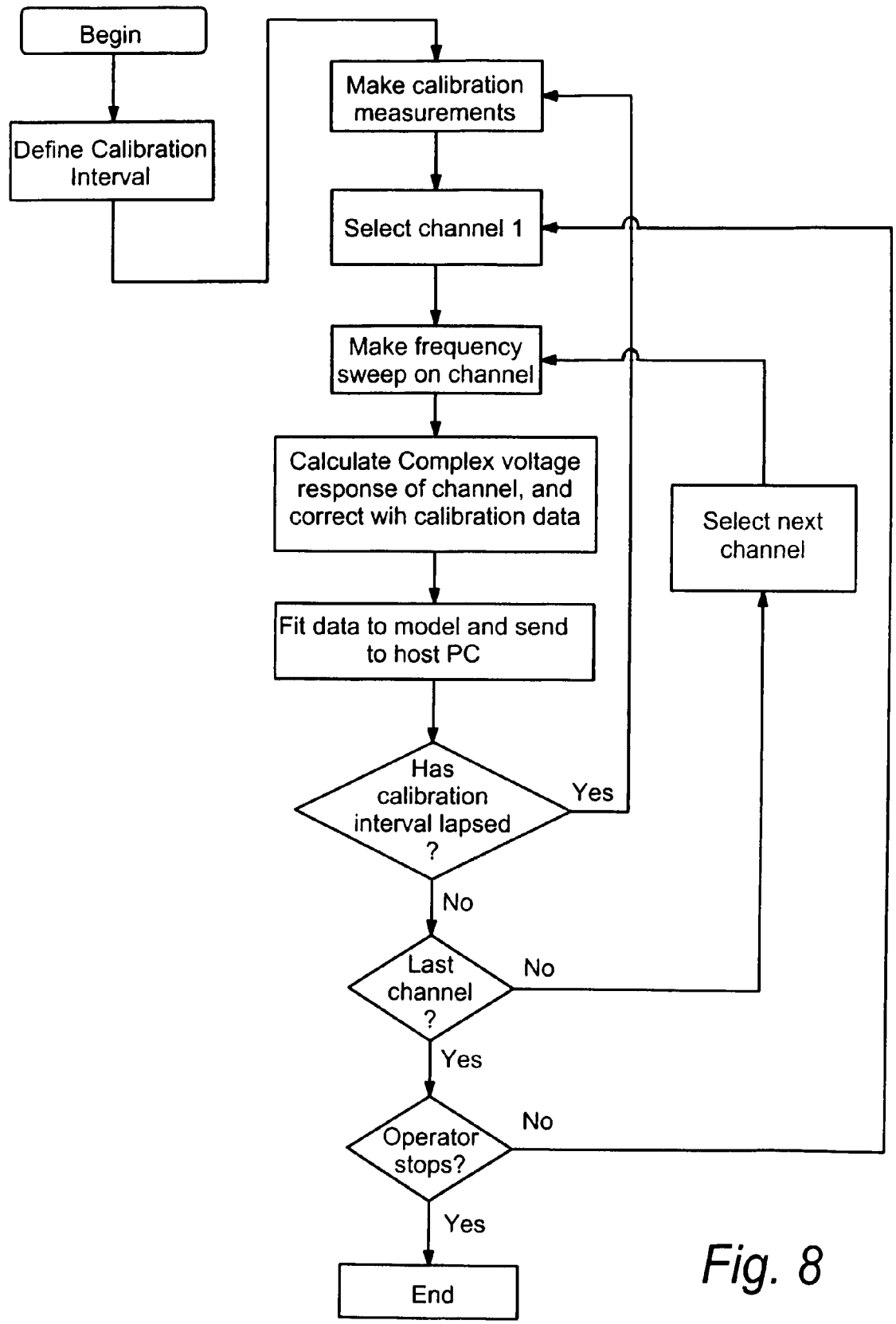
FIG. 8 is a flow chart showing the calibration process.

FIG. 8 shows the calibration process in practice. The system runs continuously until interrupted by the operator upon collection of appropriate data. The calibration interval can be set to a timescale appropriate to the instrument, and the measurement. During each calibration measurement the instrument measures the three parameters $V_{OC}$, $V_{LC}$, and $V_{SC}$. This data is used to correct the measured values of the sensor voltage $V_X$ to obtain the true admittance of the sensor element after each measurement using the transformations. The instrument can be recalibrated after any appropriate interval, either within the measurement of the sensor array, or after a complete set of elements is measured. The real and imaginary parts of the impedance (=1/admittance) correspond to the resistive and inductive load on the quartz crystal, which can be used to obtain the attached mass and the viscoelastic properties of the fluids by well known means FIG. 7 shows an alternative arrangement of sensors, calibration elements and interface to the components 1 and 4 of FIGS. 2 and 3. In FIG. 7, elements which correspond to elements in the arrangement of FIGS. 2 and 3 are denoted by the corresponding reference numerals of FIGS. 2 and 3 raised by 100. Thus sensors 143, 144 and 145 are connected to a rail 142 which is connected to a driver and a receiver through impedance matching circuitry and an amplifier similar to the components 28 and 78 of FIG. 2.

The switching system shown would be connected at point X instead of that shown in FIG. 2.

The block 147 denotes additional sensors connected in the same way as the sensors 143-145 and three calibration elements corresponding to the calibration elements 47-49. The components denoted by the reference numerals 143, 144, 145 and 147 constitute a first group of sensors and calibration elements, each of which is connectable to an active rail 141 by a respective switch, for example switch 130, of the type shown in FIG. 4. The array of sensors and calibration elements includes a second group of sensors and calibration elements 243, 245 and 247 respectively corresponding to elements 143, 145 and 147, each connectable to a second active rail 241 via a respective switch such as switch 230. The interface 104 includes a further, group selection switch 254 connected to the input from the driver 114 via a potential divider 256.

In use, the switch 254 is used to select which of the two groups of sensors/calibration elements is to be addressed, and then each component of the selected group is addressed individually in the same way as in the arrangement of FIGS. 2 and 3. In use when sensor 143 is selected all the other channels in the group 143-147 and all the sensors in the group 243-247 are deselcted using switches shown in FIG. 4. While this happens, all the sensors that have not been selected are connected to earth by the resistor 68. The switch 254 is then used to select the other group and the process is repeated for that other group.

The topology of the sensors/calibration elements array of FIGS. 2 and 3 works effectively for a limited number of sensors, but is eventually limited by the length of transmission lines in the switching architecture relative to the electronic signal's characteristic wavelength. As the number of channels (i.e. sensors/calibration elements) increases the variation of parasitic losses amongst the resonators becomes too large to be calibrated by a single set of calibration channels. The apparatus of FIG. 7, on the other hand, uses a cascade bus topology. This cascade bus topology enables a relatively large number of sensors to be used since each group of sensors in the array has associated with it a respective set of calibration elements.

Although the introduction of an additional level of switching in the cascade bus topology increases parasitic losses, this is compensated for by the use of additional calibration elements.

A variety of other arrangements based on the cascade structure can be envisaged, for examples hierarchies of levels, or cascade structures based on rows or columns in arrays, or sub-arrays within arrays.

Other varieties of calibration elements may equally be used. The use of three points can achieve true compensation because there are three unknowns in the in the system which are subject to environment induced drift; Parasitic impedance, drive voltage and drive impedance. Use of fewer than three calibration elements, although less accurate, may be suitable for systems where stability is improved by other means.

The use of open circuit, closed circuit, and reference resistance calibration elements has the advantage of simplicity of design, reliable operation, and may thus provide the widest range of application. However other calibration elements are also possible, for example the use of reactive elements, such as reference capacitors, inductors or combinations of resistive and reactive elements in small networks, or even reference oscillators may be more suited for some particular applications.

The invention has been described in terms of its application to piezo-electric devices and in particular quartz crystals operating in transverse shear mode oscillation. However the problem of parasitic losses is shared by all measurement methods which utilise high frequency electronic drive and measurement signals. (>1 MHz). The invention may thus be applied to other types of sensor.

For example, some types of sensor ultilise the fact that the electrical response of a surface immobilised molecule to an applied voltage is described by the complex dielectric permittivity. The real part of this describes the conductance of the material and the imaginary part describes the capacitance. Even through the sensor surface is not oscillating these variables show resonant behaviour as a function of frequency analogous to acoustic effects from which it is possible to derive information on molecular conformation and binding dynamics. A system for the measurement of these effects is described in U.S. Pat. No. 5,846,708.

Figure 10:
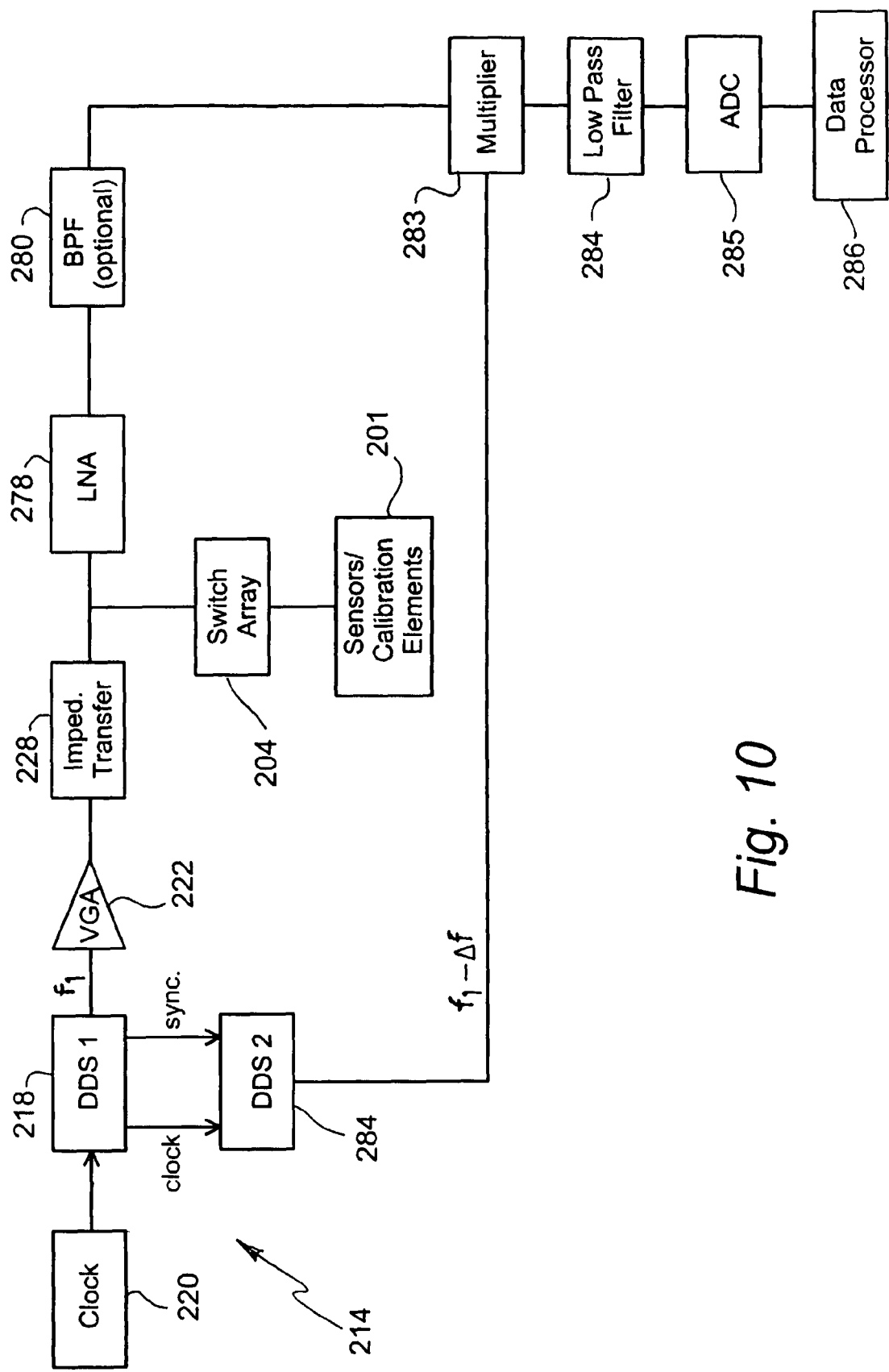
FIG. 10 is a block circuit diagram of another embodiment of apparatus in accordance with the invention.

The embodiment of analysis apparatus, in accordance with the invention, shown in FIG. 10 has a number of elements which are the same as components in the apparatus shown in FIG. 2, and are therefore denoted by the corresponding reference numerals used in FIG. 2, raised by 200. Thus the driver 214 comprises a crystal oscillator 220 which supplies a clock signal to a digital synthesiser 218. The synthesiser 218 generates a sinusoidal output frequency of a variable frequency, and this is fed to the array of sensors and calibration elements 201 via an interface 204 which includes impedance matching circuitry, a low noise amplifier and an arrangement of controllable switches for connecting the synthesiser 218 to each sensor/calibration element in turn and for relaying the signal obtained from the sensor/calibration element via the interface circuitry 204 to a multiplier 283.

The apparatus includes a second digital synthesiser 284 synchronously linked to the first digital synthesiser 218. As a result, the output of the synthesiser 284 is a sinusoidal waveform of a frequency which differs from the frequency produced by the synthesiser 218 by a constant offset. Thus the two synthesisers 218 and 284 perform a simultaneous, synchronous frequency sweep during which the frequency of the output of the synthesiser 284 always differs from that produced by the synthesiser 218 by the offset frequency.

The output of the synthesiser 284 is also fed to the multiplier 283 where the signal is mixed with the signal received from the sensor/calibration elements 201 to give an intermediate frequency signal (at a frequency equivalent to the size of the offset) which carries the phase and amplitude information of the RF signals received from the sensor/calibration elements 201. Any spurious resonant mode signal arising from transducer at frequency above the measured resonance are removed from the intermediate frequency signal by means of a low pass filter 284 before being fed to an ADC 285 therefore being supplied to a data processor 286 for analysis. The data processor 286 is also operable to control the operation of the switches in the interface 204 and the of the synthesisers 218 and 284, and corresponds to the DSP 11 of FIG. 2

In use, the drive signal is applied at a set of frequencies f which span the resonant frequency, and the detected signal at $f_i$ is mixed with an in-phase signal at $f_i-\Delta f$, where $\Delta f$ is an offset frequency. This downconverts the detected signal to the offset or intermediate frequency $\Delta f$, in which is contained the phase and amplitude information of the detected RF signal. This approach differs from conventional heterodyne methods because both the drive signal and the reference signal must maintain a precise separation ($\Delta f$) during the frequency scan. Since the intermediate signal is not DC, noise due to amplitude variation of the reference signal is eliminated, and if the detection and reference signals are in a precise phase relationship, phase jitter can be eliminated. Preferably the phase difference is zero. Because the detection signal is now encoded at a frequency A f, (1/f) noise is also eliminated.

To maintain a precision link between the drive and detection frequencies two direct digital synthesisers are used. However unless they are linked together synchronously the full noise reduction benefits of the heterodyne method are not realised. DDs's are well known in the art. In this method, the two DDS's are programmed to initiate the frequency sweep simultaneously and step through the frequency range synchronously, so that the both switch from f to f simultaneously. This can be done by providing the two DDS's with a signal clock frequency, and ultilising devices which have synchronisation inputs and outputs, to enable the simultaneous switching of frequencies. Models such as the Analog Devices AD9954 have these capabilities and are ideally suited to the application.

The FIG. 10 embodiment is also suitable for the scanning of multiple resonant frequency ranges in an array. As well as changing the resonant frequency of the fundamental mode, the attachment of mass to the transducer also causes a shift in each overtone frequency ($3^{rd}$, $5^{th}$, $7^{th}$ etc.; the even overtones not having any physical reality).

The apparatus can be used to determine all the overtone resonant frequency shifts in each sensor by scanning each element of the array at the first frequency, performing a calibration cycle, and then switching to the required overtone frequency, and repeating the cycle. A further calibration of the system is carried out at each overtone frequency used, which will be different to that at the fundamental. The process can be repeated for as many overtone frequencies as are required.

It has been found that the circuit of FIG. 2 can operate satisfactorily without the band pass filter 80, in which case this circuit can also be used to measure the overtone frequencies of the sensor resonance frequencies.

Figure 11:
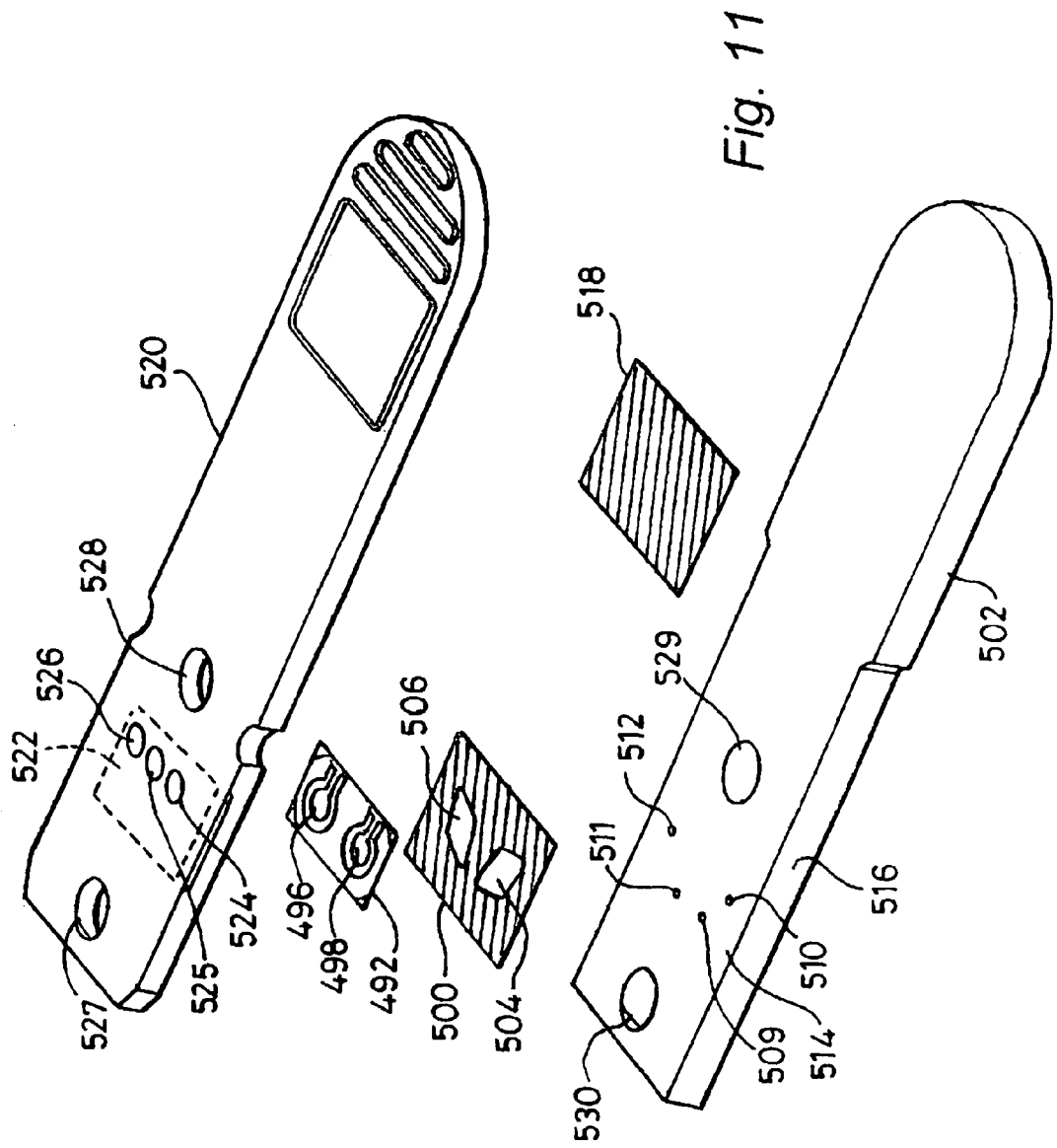
FIG. 11 is an exploded perspective view of a cartridge which provides another type of flow cell for the sensors.
Figure 12:
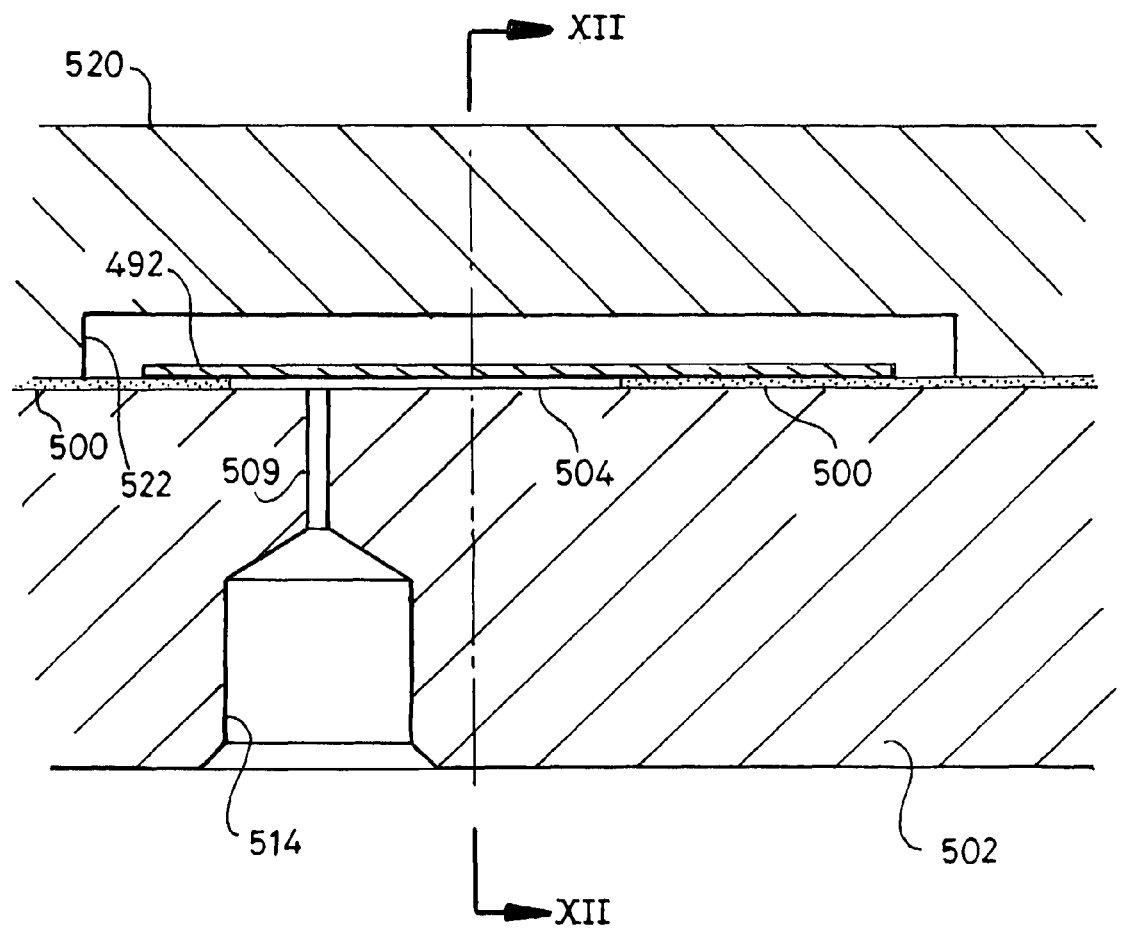
FIG. 12 is a sectional side view of the cartridge.
Figure 13:
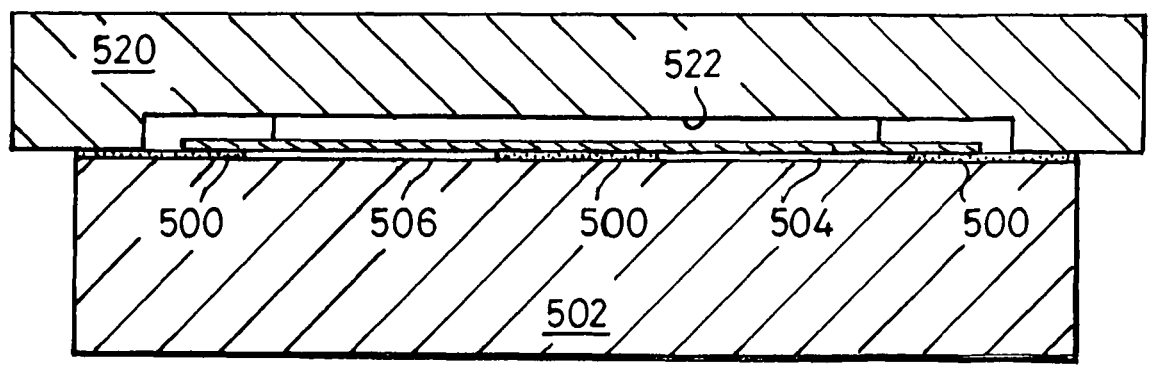
FIG. 13 is a cross-sectional view along the line XII-XII of FIG. 12.

The cartridge shown in FIGS. 11 to 13 is for use in place of the flow cell 300 shown in FIGS. 5 and 9. The cartridge defines two flow cells each of which has a respective associated sensor. The sensors are in use, connected to the switches (and hence the driver and receiver) by means of coda; ins (as described below).

A quartz crystal plate 492 forms part of the cartridge shown in the drawings. The plate is coated on one surface with gold in a pattern that defines a pair of drive electrodes 496 and 498, each of which is in registry with a respective one of two separate flow cells. The underside of the plate is also coated with gold to form a common earth electrode. A conductive track (not shown) runs from this electrode around the edge of the plate to the top surface of the plate to provide a contact for enabling a coda pin engaging the top surface of the plate to connect to the earth electrode.

The transducer 492 is adhered to the top surface of an adhesive membrane 500 the underside of which is adhered to a plate 502 the upper surface of which constitutes a support surface for the transducer 492.

The membrane 500 is a three layered structure of a total thickness of 85 microns, and comprising a polyester film carrier layer of 12 microns thickness sandwiched between two adhesive layers, each of a thickness of approximately 36.5 microns. It is possible that shrinkage of the adhesive layers occurs on curing. An example of suitable material for the membrane is the double sided adhesive tape sold under the trademark FASTOUCH. The membrane 500 has two generally diamond shaped apertures 504 and 506.

Each of the apertures 504 and 506 is in registry with a respective electrode 498 and 496, and thus with an active area of the quartz crystal. The membrane 500 spaces the transducer 492 from the upper surface of the plate 502 so that there is a small gap between each of two said active areas of the quartz crystal and the upper surface of the plate 502, each gap being bounded by the edge of a respective one of the two apertures 504 and 506. Each gap constitutes a respective flow cell which communicates with a respective pair of inlet/outlet passages 509-512 in the plate 502. Each passage leads into a female connector, such as the connectors 514 and 516 which is generally cylindrical and has a tapered end portion, each of the connectors being arranged to receive a respective ferrule of a fluid delivery/removal system.

As can be seen from FIG. 11, the inlet and outlet for each flow cell are located at opposite end regions of the latter. Consequently, a sample introduced into the inlet of the flow cell will flow along the length of the flow cell to the outlet, during which period the sample will interact with the active surface of the crystal and the effect of that interaction will be measured.

As can be seen from FIG. 11, the flow cells are situated towards one end of plate 502, towards the other end of which there is provided a patch 518 of the same material as the membrane 500. The purpose of this patch is to help to adhere a top plate 520 to the bottom plate 502. The top plate 520 includes a recess 522 which, in the assembled cartridge, accommodates the sensor 492 so that the latter makes no contact with the plate 520. The membrane 500, however, does extend beyond the boundaries of the recess 522 so as to adhere the two plates 502 and 520 together at their forward ends.

As well as securing the transducer 492 in position and defining each flow cell, the membrane 500 provides a suitable seal, by virtue of the adhesive layers, for preventing fluid escaping from the flow cells.

The upper plate, 520 includes through bores 524, 525 and 526 through which, in use, corresponding coda pins of the docking mechanism extend to make respective contact with the electrodes 96 and 98 and the earth contact of the transducer 92.

The two plates 502 and 520 also include large diameter through bores 527-530, the bore 527 in the plate 520 being in line with the bore 520 in plate 502, and the bore 528 with the bore 529 so that there are two large bore through passages in the cartridge housing (defined by the plates 502 and 520). These passages, in use, accept lateral location pins (not shown) for assisting in the correct location of the cartridge. These pins also form a Faraday cage surrounding the transducer and connection coda pins.

After a cartridge has been inserted into the docking mechanism, the ferrules on the fluidic manifold are pressed into the female fluid connectors 514, 516 in the bottom plate of the cartridge with sufficient force to cause the ferrules to deform and thereby create a fluid seal.

Then each of the coda pins extend is extended into a respective aperture 524, 525 and 526 of the cartridge upper plate 520 to engage the drive electrode or, as the case may be the earth contact on the transducer.

The plates 502 and 520 are of an engineering plastics material which is inert to biological materials. Arcylic polymers such as Polymethyl methcrylate (PMMA) amongst many known in the art are suitable.

Optionally the polymer may be coated with a material which resists fouling by biological material.

The invention claimed is:

1. Analytical apparatus for analysing at least one substance, the apparatus comprising an array of sensors, electronic drive means for operating each sensor, and a receiver for receiving and processing signals from the sensors, wherein the apparatus includes one or more calibration elements, also connected to the drive means and the receiver, for enabling changes in parasitic losses in the apparatus to be determined.

2. Apparatus according to claim 1, in which the calibration elements are such as to enable the parasitic losses, and hence any changes therein, to be determined.

3. Apparatus according to claim 1, in which the drive means and receiver are separate components of the apparatus.

4. Apparatus according to claim 1, in which each sensor comprises a respective electrical-mechanical transducer having an active surface which is oscillated by the signal from the drive means.

5. Apparatus according to claim 4, in which the apparatus is operable to measure overtone frequencies of the sensor.

6. Apparatus according to claim 4, in which the transducer comprises a piezoelectric piezo-magnetic or acoustic transducer.

7. Apparatus according to claim 4, in which, the sensor comprises a micro-electromechanical device, such as a membrane, a cantilever, a tuning fork, or other vibrating structure.

8. Apparatus according to claim 4, in which each transducer comprises a quartz crystal resonator.

9. Apparatus according to claim 4, in which the sensor has two electrodes, one of the electrodes constituting the active surface and being earthed.

10. Apparatus according to claim 4, in which each active surface carries a coating to which the one or more substances can be bound.

11. Apparatus according to claim 10, in which each coating comprises a receptor specific for the one or more substances.

12. Apparatus according to claim 1, in which the apparatus includes at least three calibration elements.

13. Apparatus according to claim 12, in which all three calibration elements are passive circuit elements.

14. Apparatus according to claim 13, in which a first of the calibration elements comprises a conductive path which provides a short circuit from the switch to earth, the second calibration element comprises an open circuit, and the third of the calibration elements comprises a resistive load of a known finite resistance.

15. Apparatus according to claim 14, in which the second calibration element comprises a gap in a conductive track from the respective switch to earth, the track corresponding to conductive tracks connecting the sensors and the other calibration elements between the switches and earth, and therefore generating parasitic losses corresponding to those associated with the interface with the other calibration elements and the sensors.

16. Apparatus according to claim 1, in which the conductive paths from the driver to the calibration elements and the sensors are preferably of substantially the same length as each other, the calibration elements and sensors thereby being situated at electrically analogous positions.

17. Apparatus according to claim 16, in which the conductive paths from each calibration element and each sensor to earth are also substantially the same length as each other.

18. Apparatus according to claim 17, in which the drive means is operable to cause the oscillation frequency of each sensor to be swept through the resonance frequency of the sensor the receiver being operable to monitor the admittance of the sensor over that range.

19. Apparatus according to claim 1, in which the drive means is operable to drive each sensor at frequencies distributed over a range of possible frequencies, the receiver being operable to monitor a characteristic of the sensor over said range.

20. Apparatus according to claim 19, in which the drive means, in use, progressively varies said frequency over said range.

21. Apparatus according to claim 19, in which the apparatus includes a signal processor wherein the signal processor is so arranged that prior to the analysis of the substance to be analysed by the sensor, the signal causes the drive means and the receiver to determine, for each sensor, a respective range of frequencies which includes the resonance frequency, or a range which includes an overtone of the resonance frequency for that sensor, the signal processor also being arranged subsequently to cause each sensor to be driven at frequencies distributed over that range in the course of said analysis.

22. Apparatus according to claim 19, wherein the sensors have associated differing ranges of frequencies which include the resonance frequencies, or a given overtone thereof, for the sensor when not analysing said substance, the apparatus being so arranged that, during the calibration, the apparatus measures the impedances of the calibration elements at frequencies distributed over a calibration range from the collective minimum to the collective maximum of the ranges associated with the resonance frequencies of the overtone frequencies of sensors.

23. Apparatus according to claim 22, in which, if there is no impedance reading for the calibration elements at a frequency at which a sensor is to be driven, the apparatus is operable to interpolate the impedance readings for the calibration elements to obtain calibration data for that frequency.

24. Apparatus according to claim 23, in which the apparatus is operable to obtain the same number of points of calibration data, over said calibration range, from each calibration element as points of impedance data for each sensor over the respective range for that sensor.

25. Apparatus according to claim 1, in which the drive means comprises a common driver operable to provide power to the sensors and the calibration elements.

26. Apparatus according to claim 25, in which the apparatus additionally comprises a plurality of switches for enabling each sensor and each calibration element to be individually addressed by the driver and receiver.

27. Apparatus according to claim 26, in which the driver and receiver are connected to the sensors and the calibration elements via a common interface.

28. Apparatus according to claim 26 in which each calibration element and each sensor is connected by the driver by a respective switch.

29. Apparatus according to claim 26, in which the switches are formed as a switching circuit in physical contact with or integrated into the array.

30. Apparatus according to claim 26, in which the array of sensors is composed of a number of groups of sensors, each group being in a respective region of the array and having a respective one or more calibration elements, wherein the switches comprise one or more primary switches for selecting a group and a plurality of secondary switches for selecting a sensor or calibration element from the selected group.

31. Apparatus according to claim 30, in which each calibration element is located in the same region as the group of sensors with which it is associated.

32. A method of analysing one or more substances using the apparatus according to claim 1, the method comprising the steps of bringing the or each substance into contact with one or more sensors in an array of sensors, supplying electrical power to the sensors and receiving and analysing the signals received from the sensors, wherein the method further comprises the steps of periodically interrogating one or more calibration elements and analysing the signals received from said one or more calibration elements to provide data on at least the changes in parasitic losses in the circuitry connected to the sensors and using said data to compensate for the effects of said changes on the received output from the sensors.

33. A method according to claim 32, in which power is supplied to each sensor in turn in one cycle of operation and at least one calibration element is interrogated once each cycle.

34. A method according to claim 33, in which if the interrogation of said calibration element indicates a significant change in parasitic loss, one or more further different calibration elements are interrogated.

35. A method according to claim 34, in which the further calibration elements are interrogated in the same cycle as the first said calibration element.

* * * * *